Figure 1:
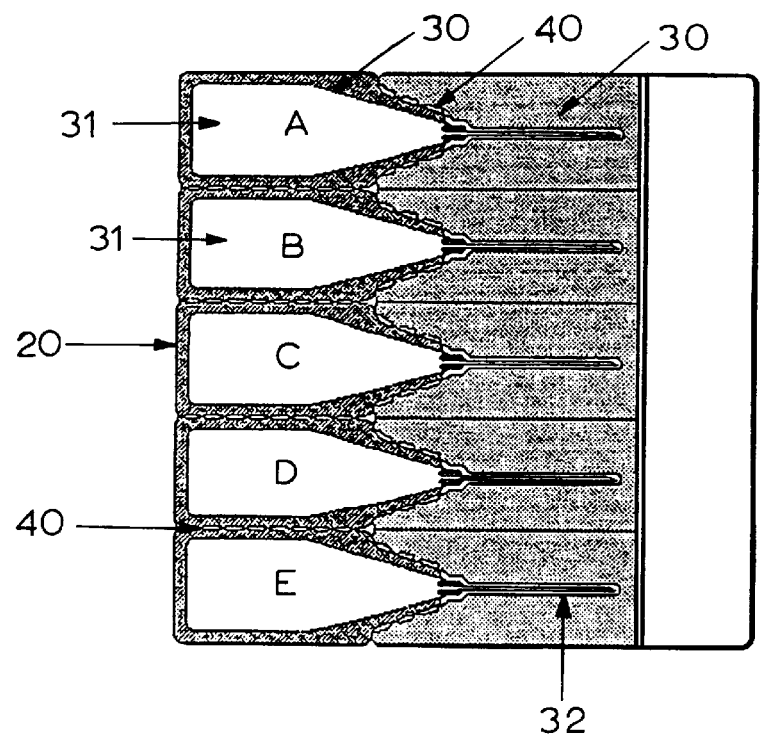

United States Patent [19]
Kahlert

[11] Patent Number: 5,873,860
[45] Date of Patent: Feb. 23, 1999

[54] INJECTION DEVICE

[75] Inventor: Ulrich Kahlert, Düsseldorf, Germany

[73] Assignee: Schwarz Pharma AG, Monheim, Germany

[21] Appl. No.: 957,089

[22] Filed: Oct. 24, 1997

[30] Foreign Application Priority Data

May 19, 1995 [DE] Germany ................. 195 18 426.2

[51] Int. Cl.[6] ................................................. A61M 5/18
[52] U.S. Cl. .................................... 604/217; 604/212
[58] Field of Search .......................... 604/216, 217, 604/212, 204, 132, 153, 272

[56] References Cited

U.S. PATENT DOCUMENTS

| | | | |
|---|---|---|---|
| 2,618,263 | 11/1952 | Lakso et al. | 128/216 |
| 3,736,933 | 6/1973 | Szabo | 128/216 |
| 3,989,045 | 11/1976 | VanEck | 128/272 |
| 4,130,117 | 12/1978 | VanEck | 128/216 |
| 5,019,048 | 5/1991 | Margolin | 604/153 |

FOREIGN PATENT DOCUMENTS

| | | |
|---|---|---|
| 1 075 283 | 2/1960 | Germany . |
| 7110309 | 3/1971 | Germany . |
| 29 00 827 A1 | 7/1980 | Germany . |
| 662 511 A5 | 10/1987 | Switzerland . |
| WO 93/09826 | 5/1993 | WIPO . |

*Primary Examiner*—John D. Yasko
*Attorney, Agent, or Firm*—Marshall, O'Toole, Gerstein, Murray & Borun

[57] ABSTRACT

The invention concerns a complete injection device which is ready for immediate use and whose injection member charged with an active substance solution and cannula form an inseparable unit. The invention also concerns a blister pack comprising at least two units, of which the basic unit is a complete injection device ready for immediate use. The advantages of the injection device are that it is a disposable syringe charged with active substance solution available for immediate use without the need of additional manipulation, remains sterile until the point immediately before use and is particularly suitable for small dosages.

2 Claims, 1 Drawing Sheet

INJECTION DEVICE

CROSS-REFERENCE TO RELATED APPLICATION

This application is a continuation of International Application No. PCT/EP96/02118, filed May 17, 1996, pending.

The present invention concerns a multiblock blister pack, which contains several independent individual basic units, in which each basic unit is a complete injection device for immediate use, consisting of the injection body and a cannula, the injection unit loaded with the active ingredient solution and the cannula forming an inseparable unit.

Injection devices, especially syringes, find many applications in daily practice. Due to their importance for solving different problems, their use extends to all technical and ethical areas of daily life.

Without claiming completeness, for example, they find use for filling the hollow spaces with different materials for accurate linear or spot gluing of individual parts or elements, but also in the food sector, for example, in the baking and confectionery industry.

In medical practice, injection devices are an essential, nonnegligible, therapeutic instruments for the treatment of different diseases in the human and veterinary area.

With this multiplicity of applications of injection devices, in the course of time, variations and different types of syringes were invented in order to take into account the special requirements for their application.

Especially in the medical area, various designs of syringes have been developed.

The type of design ranges from the conventional reusable syringe, the injection body of which is made of glass, and into which the cannula is inserted before use, to technically extensive injectors all the way to simple disposable syringes, for example, those made of plastics, which can be obtained with or without cannula. Such disposable syringes made of plastic material, as well as metal cannulas provided with a standardized adapter, are made available in so-called blister packs.

During the packaging of disposable syringes and cannulas into blister packs, the cannula is frequently inserted onto the cone of the disposable syringe ready for use. However, in these blister packs, difficulties may arise as a result of the fact that, during transport, the cannulas fall off the syringe cone or become loose. In the former case, the sterility of the syringe, as well as of the cannula, is no longer ensured upon removal from the blister. In the second case, difficulties arise when filling the solution that is to be injected, nonsterile air is filled, and liquid runs out between the cannula adapter and the syringe cone during injection.

Document DE-GBM 71 103 09.8 describes a blister pack designed as a tear-off pack, that is provided with a tab on the upper end of the pack and contains the syringe body and the cannula separately. Using the tab, the blister pack can be opened easily and is torn apart only to such an extent that the syringe body can be lifted up and the cone can be inserted into the cannula, which is also exposed just slightly. In comparison to the construction of other blister packs, this has the advantage that the syringe body and the cannula can be put together under the protection of the still-present blister packing under aseptic conditions.

However, the disadvantage that the syringe body and the cannula have to be put together before use still exists, and then, afterwards, the drug to be injected still has to be filled into the syringe. Septic problems cannot be excluded during these necessary manipulations.

From DE-AS 1 075 283, a disposable injection ampule is known in which the cannula is tightly joined to the ampule body, which is closed with a membrane. Before use, this membrane is pierced by a needle mounted in a bolt, whereupon the protective sleeve is removed and then the injection ampule is ready for use. However, the construction has the disadvantage that production of the unit consisting of many individual sleeves is expensive and the structure is complicated. Furthermore, satisfactory handling is not possible. Thus, for example, after piercing of the sealing membrane, when pulling off the closing sleeve, release of some injection solution before the syringe is ready for insertion cannot be avoided.

DE 29 00 827 A1 also describes a disposable injection ampule. It consists of an easily deformable ampule body, a cannula body with solidly adapted cannula, from which the cannula protrudes on both sides so that it can be shifted, and a removable protective cap. In this construction, the disadvantage lies in the fact that production is very expensive and that, even before use of the injection ampule, this has to be made ready for use by shifting the cannula in the ampule body. Another disadvantage in handling is that the protective cap must be removed before use. Finally, it is not ensured that the protective cap of the cannula will not fall off during transport or during handling just before use, so that the required sterility is not always ensured.

A syringe filled with a drug with a separate cannula is known from U.S. Pat. No. 3,989,045. Here, too, in an embodiment, it is disadvantageous that the ampule and the cannula are separate and that they have to be put together before use. Furthermore, as a result of this, sterility is not always ensured.

In another embodiment, the injection ampule and cannula are solidly joined together and the cannula is protected by a removable protective cap. However, the construction of this protective cap does not provide any advantages in comparison to the protective cap constructions mentioned in the documents cited above.

Document U.S. Pat. No. 4,130,117 describes an injection ampule prefilled with a drug with a separate cannula. In addition, it contains a membrane which must be removed before use. The injection ampule characterized by these structural features also has the disadvantages mentioned above, especially the expensive production, that is, the assembly of the individual parts to a ready-to-use injection ampule.

CH-P 662 511 A5 discloses a method for the preparation of an ampule filled with drugs intended to be used with a hypodermic needle. According to this method, injection ambles are produced of the type described in U.S. Pat. No. 3,989,045 and U.S. Pat. No. 4,130,117. Therefore, the injection ampules prepared accordingly have the same disadvantages as were described above.

Therefore, in order to provide sterility, the syringes should be provided as syringes ready for injection, filled with the active ingredient to be applied, produced, and packed in a sterile manner and designed as a so-called disposable syringe.

The document U.S. Pat. No. 5,019,048 describes an injection device for immediate use. Here, two congruent films 13, 14 (FIGS. 1, 2, and 7–10), welded together as mirror images, which have regions that lie against each other and regions that do not, form two pockets 56, 59 with the regions that do not lie against each other. Pocket 56 forms the injection body to be filled with the active ingredient, and is joined to a cannula 55 so that it can be swung out. The cannula 55 protrudes into a tubular end of pocket 56.

However, in the embodiments shown in FIGS. 7 and 8, it is a disadvantage that the cannula must be taken out from the narrow, elongated pocket 59, which lies against the pocket 56 that forms the injection body, with the aid of shearing forces being transferred to the injection body, and, moreover, must be swung out for use. In order to permit this, the film material used must be very pliable, so that no damage would occur to pocket 56 when the cannula is swung out.

Furthermore, it is a disadvantage that when the cannula is inserted into the body of a patient, the forces required for such insertion act not only in the direction of insertion, but perpendicular to it, too, since the cannula is attached in one corner of the injection body which is designed in the form of a rectangle or square.

The handling of such a construction is devoid of the required compliance and inevitably causes unnecessary pain to the patient.

Figure 2:
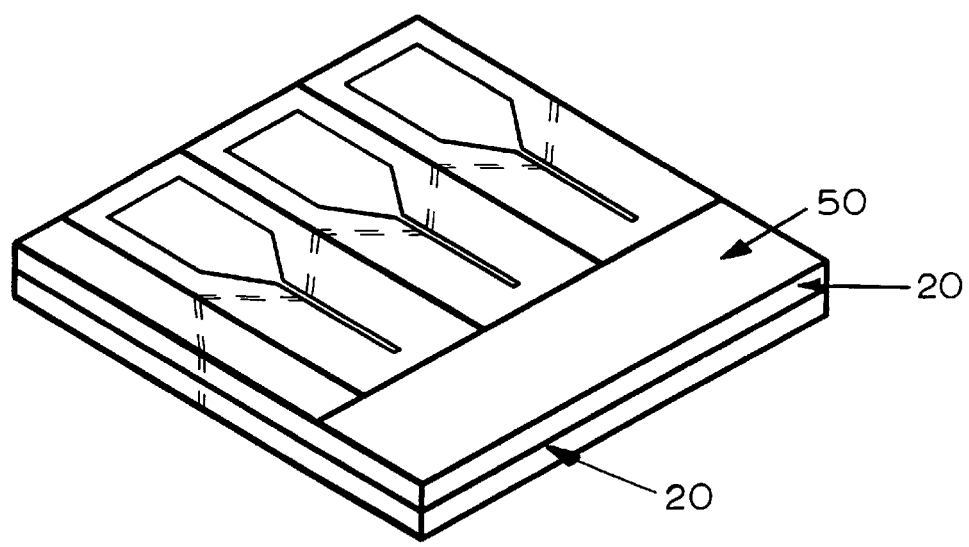

One can see in FIGS. 1 and 2 of this document an injection device with a very complicated design, which should serve as a disposable article.

According to this, due to the design, the injection needle must be turned in the direction of application before use of the injection device, with the aid of a disk contained in the device.

First of all, any additional body in a device containing a sterile material represents a foreign body, which is to be avoided for reasons of toxicity. Furthermore, such a design is complicated and the manufacturing technology is expensive. These are characteristics that a disposable article should not have, since then the realization is cost-intensive.

Although FIGS. 3 and 4 of this document do not show a rotatable disk with which the cannula has to be moved, but a rotating joint is necessary to bring the cannula in the injection direction before use. Thus, again, an additional manipulation is necessary before use, quite apart from the fact that the design of the additional rotating joint is complicated and is expensive to manufacture. Another design disadvantage of this arrangement of the injection body and the injection needle is that during injection of the contents of such a device the force vector cannot work in one direction, which again leads to undesirable pain of the patient.

Finally, FIGS. 10 and 11 show an injection device as one unit of several in a multiblock blister pack, which has holes on the side edges, which serve for transport through a specially designed tool, namely a vaccination gun (120). The disadvantage here is that the individual units of these multiblock blister packs are not available to the use per se, but only by pulling through a special tool designed for this purpose, namely the vaccination gun. This is not only complicated and expensive, but also involves increased manipulations.

Finally, an increased packaging and space requirement are involved here, which is undesirable for the storage and transport of industrially manufactured products.

Finally, the individual units of this multiblock blister pack necessarily involve the disadvantages discussed above, such as a cannula which is to be rotated with a disk.

This is a very complicated and, thus, expensive design for a single-use disposable syringe.

Injection devices should be able to be handled without problems and yet safely, should be available not only to the treating physician, but also to the patient, for safe self-medication, and should have a simple structure that permits cost-effective manufacture.

The task of the invention is to make available an injection device having the above advantages.

Surprisingly, it was possible to make available an injection device for immediate use, preloaded with the drug to be injected, in the form of a multiblock blister pack, consisting of several individual units, in which the basic unit is a complete injection device, consisting of the injection body and a cannula, for immediate use as a disposable syringe and which has characteristics listed below.

Therefore, the invention is concerned with a multiblock blister pack, in which a complete injection device for immediate use is present, the syringe body of which is filled with the particular drug to be injected forms with the cannula a nonseparable unit in the injection direction, which itself is a component of the multiblock blister pack as a basic unit.

Hereby, the syringe body of the injection device is produced by two congruent films, which are welded together in a mirror-image manner and represent parts that do not lie against each other, but form a pocket which is filled with the particular active ingredient. This is adjoined on the cannula, which protrudes into the above pocket on one end, forming a nonseparable unit with it, solidly bonded to it, the remaining part of it protrudes into another pocket which is also made of the two congruent films mentioned above that are welded together in a mirror-image fashion.

The injection device is designed in such a way that the syringe body is made of a material that can be deformed under pressure. Finally, the syringe body itself forms the package.

According to another embodiment of the invention, the injection device can be separated into a basic unit from a unit of at least two units bonded together forming a multiblock blister unit. Preferably, a multiblock blister unit contains five to ten units of the injection device.

For this purpose, multiblock blister units are provided with suitable perforations which make the separation of a ready-to-use unit from the whole block possible.

The multiblock blister pack, according to the invention, has the following embodiment.

It is formed from two congruent films (20), which are welded together in a mirror-image fashion and have areas (30) lying against one another, as well as areas that do not lie against one another and form hollow spaces (31), thus forming two pockets. One pocket (for example, A(31)) represents the syringe body and is filled with the active ingredient to be injected. Its part facing the cannula is formed in a conical fashion into which the cannula penetrates, joined with the pocket on one end of defined length that represents the fixed connection. This pocket has welded seams all around it and has perforations on the sides away from the pocket (40), as long as the welding edges are inside. These perforations or areas to be broken permit removal, from the multiblock blister pack, of the syringe body with the solidly attached cannula as a complete injection device for immediate use.

The other, elongated pocket (32) holds the cannula. When separating the syringe body from the multiblock blister pack, the cannula, which is solidly attached to the syringe body, slides out from the pocket, which represents a protective packaging for the cannula.

A welded edge (50) runs along the entire length of the multiblock blister pack on the side that faces the cannulas, and this welded seam can be made stronger and is supposed to facilitate the separation of the injection device by providing additional holding.

The attached drawings explain the invention in more detail.

FIG. 1 is a top view of five injection devices lying next to one another in a multiblock blister pack.

The letters A–E show the syringe bodies designed as pockets (31), which are formed from two congruent films (20) that are welded together in a mirror-image manner and filled with active ingredients. The hollow spaces that form pockets (31) and (32) are separated by areas lying against one another (30), which surround the syringe body. This is adjoined on elongated pockets (32) intended for holding the cannulas.

The perforations (40), where the break is supposed to take place, run along the edges of the syringe bodies; these edges are always on the inside and make it possible to separate the particular injection device.

FIG. 2 shows a three-dimensional representation of the invention with a top view and a side view. The congruent films that are welded together in a mirror-image manner are shown by (20). The preferably reinforced edge, which is also present for separation, is shown by (50).

The injection devices as parts of the multiblock blister pack are made of plastic material, preferably polyethylene, polypropylene, polyvinyl chloride, or polystyrene.

The injection device is suitable in a special way, without being restricted to this, for administration of "small volume parenterals." They are especially suitable for intramuscular or subcutaneous self-medication. However, it is also intended for intravenous administration of drugs.

As active ingredients, all active ingredients come into consideration which are suitable for administration by injection.

The capacity of the syringe body described according to the invention ranges from 0.1 mL to 30 mL, preferably from 0.1 mL to 1 mL.

The solid joint of the injection body with the cannula can be achieved by adhesion, welding, crimping, or shrinking.

Fundamentally, the blow-molding technology, also called "Blow-Fill-Seal Technology" (BFS Technology), can be used for the production of the injection device, especially the injection body according to the invention.

This blow-fill-seal technology excels at the present time as a suitable aseptic packaging method with which the desired form is first blown and then filled with the sterile contents and finally sealed in one process.

The essential process steps of this technology have been described in the company brochures of Waverley Pharmaceutical, Cheshire WA7 1QE, England, and Automatic Liquid Packaging, Inc. (ALP), Woodstock, Ill. 60098, U.S.A.

What is claimed is:

1. A multiblock blister pack comprising a plurality of independent individual basic units, wherein each basic unit is a finished injection device for immediate use, in the form of a multiblock blister pack of two congruent films joined together in a mirror-image manner with hollow spaces formed as pockets, characterized by the fact that the pack comprises at least two injection devices, each of which is an independent individual basic unit of a plurality of units in the multiblock blister pack, wherein each basic unit is formed from two congruent films (20), joined together in a mirror-image manner, having areas which lie against each other (30), and areas separated from each other (31) to form two pockets with areas that do not lie against each other, wherein one pocket is an injection body, filled with active ingredient, and having a conical end with one end of a cannula solidly bonded to the conical end and penetrating into the conical end, and the remaining cannula part of a defined length protruding into the second, elongated pocket for protective holding, and, along the sides away from the injection body, which has welded edges surrounding the pocket of the injection body, as long as they lie inside, has perforations (40), which make it possible to separate a basic unit from the pack with simultaneous exposure of the cannula without any interfering protective shell, for immediate use, as well as another edge (50) formed by the welded seam over the entire length of the side of the multiblock blister pack facing the cannula.

2. The multiblock blister pack of claim 1 wherein the reinforced edge extending over the entire length of the side of multiblock blister pack facing the cannulas is at least 10 mm wide.

* * * * *